(12) United States Patent
Feng

(10) Patent No.: US 7,871,634 B2
(45) Date of Patent: Jan. 18, 2011

(54) COSMETIC COMPOSITIONS USEFUL FOR LENGTHENING LASHES

(75) Inventor: Sue Feng, Edison, NJ (US)

(73) Assignee: L'Oréal (FR)

( * ) Notice: Subject to any disclaimer, the term of this patent is extended or adjusted under 35 U.S.C. 154(b) by 247 days.

(21) Appl. No.: 11/201,732

(22) Filed: Aug. 11, 2005

(65) Prior Publication Data

US 2007/0036739 A1 Feb. 15, 2007

(51) Int. Cl.
*A61Q 5/00* (2006.01)
*A61Q 5/06* (2006.01)
*A61K 8/02* (2006.01)

(52) U.S. Cl. .................. 424/401; 424/70.11; 424/70.16; 514/937

(58) Field of Classification Search .................. 424/401, 424/70.11, 70.16; 514/937
See application file for complete search history.

(56) References Cited

U.S. PATENT DOCUMENTS

| | | | |
|---|---|---|---|
| 4,871,536 A | 10/1989 | Arraudeau et al. | |
| 5,651,979 A | 7/1997 | Ron et al. | |
| 5,783,657 A | 7/1998 | Pavlin et al. | |
| 5,840,338 A | 11/1998 | Roos et al. | |
| 5,876,741 A | 3/1999 | Ron | |
| 5,939,485 A | 8/1999 | Bromberg et al. | |
| 6,001,367 A | 12/1999 | Bazin et al. | |
| 6,251,954 B1 | 6/2001 | Roulier et al. | |
| 6,338,839 B1 | 1/2002 | Auguste et al. | |
| 6,375,941 B1 | 4/2002 | Piot | |
| 6,402,408 B1 * | 6/2002 | Ferrari | ............ 401/64 |
| 6,413,526 B1 | 7/2002 | Bazin et al. | |
| 6,482,400 B1 | 11/2002 | Collin | |
| 6,534,047 B1 | 3/2003 | Bodelin | |
| 6,726,917 B2 | 4/2004 | Kanji et al. | |
| 2001/0028887 A1 | 10/2001 | Douin et al. | |
| 2001/0033826 A1 | 10/2001 | Roulier et al. | |
| 2002/0028226 A1 | 3/2002 | Terren et al. | |
| 2002/0034524 A1 * | 3/2002 | Poret | ............ 424/401 |
| 2002/0168335 A1 | 11/2002 | Collin | |
| 2003/0003064 A1 | 1/2003 | Kalla et al. | |
| 2003/0003065 A1 | 1/2003 | Kalla et al. | |
| 2003/0012764 A1 | 1/2003 | Collin | |
| 2003/0064038 A1 * | 4/2003 | Auguste et al. | ............ 424/63 |
| 2003/0215413 A1 | 11/2003 | Fares et al. | |
| 2003/0215476 A1 | 11/2003 | Cassin et al. | |
| 2003/0235553 A1 | 12/2003 | Lu et al. | |
| 2004/0136937 A1 | 7/2004 | Cassin | |
| 2004/0142831 A1 | 7/2004 | Jager Lezer | |

FOREIGN PATENT DOCUMENTS

| | | |
|---|---|---|
| EP | 0596550 A2 | 5/1994 |
| EP | 1008340 AZ | 7/1999 |
| EP | 1043345 A | 3/2000 |
| EP | 1419763 | 10/2003 |
| FR | 2659551 | 3/1991 |
| FR | 2821744 | 9/2001 |
| FR | 2843025 | 2/2004 |
| JP | 10298051 | 11/1998 |
| JP | 2000086491 | 3/2000 |
| JP | 2000128738 | 5/2000 |
| JP | 2000191444 | 7/2000 |
| JP | 2000273028 | 10/2000 |
| JP | 2000297027 | 10/2000 |
| WO | WO-96/02276 | 2/1996 |
| WO | WO-98/29092 A1 | 7/1998 |
| WO | WO-98/48768 | 11/1998 |
| WO | WO-03/042221 | 5/2003 |

OTHER PUBLICATIONS

Galgoci et al., http://www.airproducts.com/NR/rdonlyres/875C48B4-21A6-4FF4-B94C-40480EF2C9F2/0/ERFpaper401.pdf, 2001, 15 pages.*
Fragrance Journal, Aug. 1998, pp. 79-83.
European Search Report, 06254197, dated Jun. 17, 2008.

* cited by examiner

*Primary Examiner*—Johann R Richter
*Assistant Examiner*—Abigail Fisher
(74) *Attorney, Agent, or Firm*—Lerner, David, Littenberg, Krumholz & Mentlik, LLP

(57) ABSTRACT

Disclosed are mascara compositions containing an aqueous phase, fatty phase, a structuring agent, and a polyurethane/poly(meth)acrylate graft copolymer, and methods of making and using them.

20 Claims, No Drawings

COSMETIC COMPOSITIONS USEFUL FOR LENGTHENING LASHES

BACKGROUND OF THE INVENTION

The cosmetic industry focuses much of its efforts, in regards to mascara, on increasing length and volume or thickness of eyelashes, and extending length of wear.

U.S. Pat. No. 6,375,941 teaches wax-free mascara compositions containing an aqueous dispersion of particles of a film-forming polyurethane, and which has a viscosity, measured at 25° C., at a shear rate of 200 $s^{-1}$, ranging from 5 Pa·s to 18 Pa·s.

U.S. Pat. No. 6,482,400 teaches cosmetic compositions for coating keratin fibers, containing a cationic polymer, an anionic polymer and an aqueous polyurethane dispersion. U.S. Pat. No. 6,534,047 teaches cosmetic compositions for coating keratin fibers, containing a cationic polymer, an anionic polymer and an aqueous dispersion of a $C_1$-$C_6$ alkyl (meth)acrylate. The patents teach that the compositions lead rapidly to a uniform make-up result that have good properties of coating, lengthening and curling the eyelashes, as well as good staying power.

U.S. Pat. No. 6,726,917 teaches mascara for providing volume and/or length to eyelashes, containing fibers, pigments, and at least two film formers: at least one tacky film former soluble or dispersible in water; and at least one tacky film former soluble in oil chosen from hydrogenated polyisobutenes, adipic acid/diethylene glycol/glycerin crosspolymers, polyethylenes, and polyvinyl laurates.

SUMMARY OF THE INVENTION

A first aspect of the present invention is directed to a mascara composition comprising an aqueous phase, a fatty phase, a structuring agent, and a polyurethane/poly(meth)acrylate graft copolymer. Methods of making the mascara are also provided.

A second aspect of the present invention is directed to a method of lengthening eye-lashes, comprising applying to eye-lashes a mascara composition comprising an aqueous phase, a fatty phase, a structuring agent, and a polyurethane/poly(meth)acrylate graft copolymer.

Applicants have discovered that mascara of the present invention, when applied to eyelashes, lengthen the eyelashes. Compositions of the present invention may offer one or more additional advantages such as greater softness and evenness of film deposited on the lashes, improved separation and longer wear.

DETAILED DESCRIPTION OF THE INVENTION

Mascara may be formulated as washable or waterproof. The term washable mascara, as used herein, refers to compositions that may be removed with water and/or soap. These formulations are typically emulsions (e.g., of waxes in water) such as creams, or in some cases gels and cakes. Waterproof mascara, which require use of oils for removal, generally, comes in the form of dispersions of waxes in organic solvents, e.g., isododecane and petroleum distillate.

The polyurethane/poly(meth)acrylate graft copolymers may also be referred to as an interpenetrated polymer network (IPN) of a polyurethane and a poly(meth)acrylate. As used herein, the expression "interpenetrated polymer network" refers to a blend of two interlaced polymers, obtained by simultaneous polymerization and/or crosslinking of two types of monomer, the blend obtained having a single glass transition temperature. Such IPNs are especially those that are commercially available from the company Air Products under the name Hybridur. An IPN that is particularly preferred is in the form of an aqueous dispersion of particles e.g., with a weight-average size of between 90 and 110 nm and a number-average size of about 80 nm. This IPN preferably has a glass transition temperature, Tg, ranging from about −60° C. to +100° C. An IPN of this type is available from Air Products under the trade name Hybridur 875 (INCI name: POLYURETHANE-2 (and) POLYMETHYL METHACRYLATE). Polyurethane/poly(meth)acrylics available from Air Products under the names Hybridur X-01602 and X 18693-21 are also disclosed in U.S. Publication Nos. 2003/0215476 and 2004/0136937.

The IPNs of the present invention are polyurethane/poly(meth)acrylate graft copolymers having the following general structure:

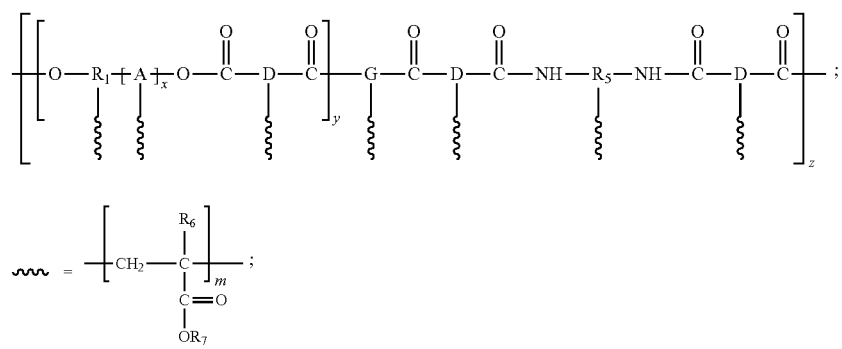

wherein

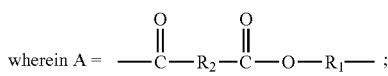

wherein D = —NH—$R_3$—NH—;

and wherein

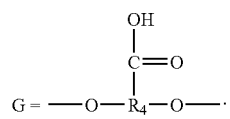

In the formula, $R_1$, $R_2$, $R_3$, $R_4$, $R_5$ and $R_7$ each independently represents an aliphatic hydrocarbon; m represents zero or a positive integer; $R_6$ represents hydrogen or methyl; and x, y and z each independently represents a positive integer. The graft copolymers may be provided in the form of aqueous dispersions. The graft copolymers may be added to the other components of the mascara in powdered form as well.

The IPN of polyurethane/poly(meth)acrylate (or polyurethane/poly(meth)acrylate graft copolymer) is present in the mascara of the present invention in an amount generally ranging from about 0.01 to about 20% by weight of the copolymer, preferably from about 0.5% to about 15% by weight, and more preferably from about 1% to about 5% by weight, relative to the total weight of the composition.

The compositions of the invention contain a cosmetically acceptable carrier. The carrier contains a fatty phase and an aqueous phase. The fatty phase typically contains one or more of fatty substances chosen from oils, organic solvents, structuring agents such as waxes and structuring polymers, pasty fatty substances and mixtures thereof.

As disclosed herein, the term "liquid fatty phase" means refers to a non-aqueous medium that is liquid at room temperature (25° C.) and atmospheric pressure (760 mmHg, i.e., 105 Pa), comprising at least oil or oily liquid that are in general, are mutually compatible. Oily (oil soluble) liquids are included in the compositions of the present invention to provide desirable feel, spreadability, and/or other desirable characteristics. The inventive compositions may contain any cosmetically or dermatologically acceptable oil, chosen in particular from carbon-based, hydrocarbon-based, fluoro and/or silicone oils, of mineral, animal, plant or synthetic origin, alone or as a mixture, provided that they form a homogeneous and stable mixture and provided that they are compatible with the intended use.

The term "hydrocarbon-based oil" means an oil mainly comprising carbon and hydrogen atoms and possibly at least one functional group chosen from hydroxyl, ester, ether and carboxylic functional groups. For example, the oils may have a viscosity ranging from 0.5 to 300,000 centipoise (cps), further for example, from 50 to 50,000 cps, and even further for example, from 100 to 100,000 cps. Examples of hydrocarbon-based oils include the following: hydrocarbon-based oils of animal origin, such as perhydrosqualene; hydrocarbon-based plant oils such as liquid triglycerides of fatty acids of from 4 to 24 carbon atoms, for instance heptanoic or octanoic acid triglyceride, or alternatively sunflower oil, maize oil, soybean oil, marrow oil, grapeseed oil, sesame seed oil, hazelnut oil, apricot oil, macadamia oil, castor oil, avocado oil, caprylic/capric acid triglycerides, for instance those sold by the company Stearineries Dubois or those sold by the company Dynamit Nobel under the names Miglyol 810, 812 and 818, jojoba oil and shea butter; linear and branched hydrocarbons of mineral or synthetic origin, for example, liquid paraffin and derivatives thereof, petroleum jelly, polydecenes, polybutenes and hydrogenated polyisobutene, for example Parleam™; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononanoate, 2-ethylhexyl palmitate, 2-hexyldecyl laurate, 2-octyldecyl palmitate, 2-octyldodecyl myristate or lactate, 2-octyldodecyl stearate, 2-octyldodecyl erucate, bis(2-ethylhexyl) succinate, diisostearyl malate, glyceryl triisostearate or diglyceryl triisostearate, isopropyl myristate, isostearyl isostearate and tridecyl trimellitate; higher fatty acids, such as myristic acid, palmitic acid, stearic acid, behenic acid, oleic acid, linoleic acid, linolenic acid or isostearic acid; higher fatty alcohols (e.g., having from 10-26 carbon atoms) such as ketanol, stearyl alcohol, oleyl alcohol, linoleyl alcohol, linolenyl alcohol, isostearyl alcohol or octyldodecanol; hydroxylated esters, for instance isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate.

The oils may include volatile and non-volatile oils. The volatility of the solvents/oils can be determined using the evaporation speed as set forth in U.S. Pat. No. 6,338,839. The inventive compositions may contain one or more volatile silicone oils. Examples of such volatile silicone oils include linear or cyclic silicone oils having a viscosity at room temperature less than or equal to 6 centistokes (cSt) and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils that may be used include KF 96A of 6 cSt viscosity, a dimethylpolysiloxane commercial product from Shin Etsu having a flash point of 94° C. Suitable volatile linear silicone oils include those described in U.S. Pat. No. 6,338,839 and International Patent Publication WO 03/042221. Preferably, the volatile silicone oils have a flash point of at least 40° C. Non-limiting examples of volatile silicone oils are listed in Table 1 below.

TABLE 1

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5cSt) from Dow Corning | 56 | 1.5 |
| PDMS DC 200 (2cSt) from Dow Corning | 87 | 2 |
| PDMS DC 200 (5cSt) from Dow Corning | 134 | 5 |
| PDMS DC 200 (3St) from Dow Corning | 102 | 3 |

Examples of other silicone oils that may be used in the invention include the following: non-volatile linear polydimethylsiloxanes (PDMSs) that are liquid at room temperature; polydimethylsiloxanes that may be substituted with fluoro groups, functional groups such as hydroxyl, thiol or amine groups, aliphatic (e.g., alkyl) groups or aromatic (e.g., phenyl) groups, which are pendent and/or at the end of a silicone chain, these groups each containing from 2 to 24 carbon atoms; phenylsilicones, for instance phenyl trimethicones, phenyl dimethicones, trimethyl pentaphenyl trisiloxane, tetramethyl tetraphenyl trisiloxane, phenyl trimethylsiloxydiphenylsiloxanes (e.g., DC555 from Dow Corning), diphenyl dimethicones, diphenyl methyldiphenyl trisiloxanes and 2-phenylethyl trimethylsiloxysilicates. Other examples of silicone oils include polysiloxanes modified with fatty acids, fatty alcohols or polyoxyalkylenes, fluorosilicates and perfluoro oils.

The composition may contain one or more non-silicone volatile oils such as volatile hydrocarbon oils, alcohols, volatile esters and volatile ethers. Examples of such volatile non-silicone oils include volatile hydrocarbon oils having from 8 to 16 carbon atoms and their mixtures, and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, and their mixtures. In some embodiments, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Isohexadecane | 102 |
| Isodecyl Neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Low viscosity oils (generally from about 5 or 10 centipoise (cps) at 25° C., and up to about 100 cps, preferably up to about 50 cps, at 25 ° C.), high viscosity oils (at least about 100 cps, preferably at least about 150 cps (at 25° C.) and up to about 10,000, preferably up to about 1,000 cps (at 25° C.)), and mixtures thereof can be used. Representative low viscosity oils (viscosity in the range of 5-15 cps at 25° C.) include isononyl isononanoate, octyl palmitate, diioctylmaleate, octyldodecanol, PEG-4 diheptanoate, isononylnonanoate, coco -dicaprylate/caprate, polyglyceryl-3-diisostearate, cetyl alcohol, isocetyl alcohol, oleyl alcohol, cetyl acetate, acetylated lanolin alcohol, and the like. Examples of high viscosity oils (viscosity in the range of 100-1,000 cps at 25° C.) include lanolin oil, sesame seed oil, glyceryl trioctanoate, tridecyl trimellitate, castor oil, caprylic/capric triglyceride, corn oil, mineral oil, hydrogenated polyisobutene, polybutene polyvinylpyrrolidone (PVP)/hexadecene, diisoarachidyl dilinoleate, diisopropyl malate (DISM) and trioctyldodecyl citrate.

Amounts of oil in the cosmetic compositions of the present invention generally ranges from about 1.0 to about 40% by weight, and in some embodiments is about 5.0 to about 20% by weight.

The compositions of the present invention may contain a structuring agent. As used herein, the term "structuring agent" refers to an agent, which is not an oil, but rather is (or contains) a solid or semi-solid (at room temperature), and in preferred embodiments, is a wax or a non-wax polymer, that will at least thicken the liquid fatty phase.

In some embodiments, the structuring agent includes at least one wax. For the purposes of the present invention, the term "wax" means a lipophilic fatty compound that is solid at room temperature (25° C.) and atmospheric pressure (760 mmHg, i.e. $10^5$ Pa), which undergoes a reversible solid/liquid change of state and which has a melting point of greater than 30° C. and in some embodiments, greater than 55° C. up to 120° C. or even as high as 200° C.

For the purposes of the invention, the waxes are those generally used in cosmetics and dermatology. A variety of waxes may be useful, including waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candellila wax, ouricurry wax, cork fibre waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes. Alternatively, hydrogenated oils of animal or plant origin may be used. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils. In some embodiments, the compositions contain at least two waxes.

In some embodiments, the wax has a low melting point, generally ranging from about 35-70° C., but unlike such low MP waxes, has a hardness (e.g., generally about 7-10 mm/10, as measured in accordance with ASTM-D1321) that is associated with waxes having high melting points. Such waxes are commercially available from Mineral and Pigment Solutions, Inc. or Koster Keunen under the name BK, e.g., BK-42 (INCI tetradecyl octadecanyl-behenate; CAS No.:231627-84-2; $C_{54}H_{108}O_2$) and BK-60 (INCI name: hexadecyl-cosanyl-hecacosanate; $C_{62}H_{124}O_2$).

The wax may be present in the compositions in an amount generally ranging from about 0.1% to about 40%, preferably from about 0.5% to about 20%, and more preferably from about 1% to about 10% by weight, relative to the total weight of the composition.

The compositions of the present invention may contain a structuring agent comprising a non-wax polymer. Examples of suitable structuring polymers are disclosed in U.S. Pat. Nos. 5,783,657 and 6,402,408. Specifically, the disclosed polymers are ester-terminated polyamides represented by the following formula (II):

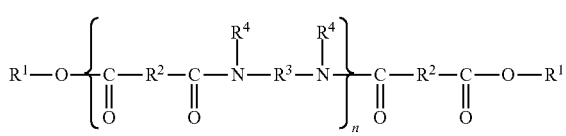

in which:

n is an integer which represents the number of amide units such that the number of ester groups present in the structuring polymer ranges from 10% to 50% of the total number of all the ester groups and all the amide groups comprised in the structuring polymer (e.g., n may be an integer ranging from 1 to 5, for example, an integer ranging from 3 to 5);

$R^1$, which are identical or different, are each chosen from alkyl groups comprising at least 4 carbon atoms and alkenyl groups comprising at least 4 carbon atoms (e.g., each can be chosen from $C_{12}$ to $C_{22}$ alkyl groups, such as from $C_{16}$ to $C_{22}$ alkyl groups);

$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to group chosen from $R^3$ and another $R^4$ such that when the at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In one embodiment, the at least one terminal fatty chain of formula (II) is linked to the last hetero-atom, in this case nitrogen, of the polyamide skeleton. In a further embodiment, the terminal chains are functionalized. In another embodiment, the ester groups of formula (II) are linked to the terminal and/or pendant fatty chains, represent from 15% to 40% of the total number of ester and amide groups, such as, for example, from 20% to 35%.

In the present invention, $R^2$, which are identical or different, can, for example, each be chosen from $C_{10}$ to $C_{42}$ alkyl groups. At least 50% of all $R^2$, which are identical or different, can, for example, each be chosen from groups comprising from 30 to 42 carbon atoms. At least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{19}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each be chosen from $C_2$ to $C_{12}$ hydrocarbon-based groups. In another embodiment, $R^4$, which can be identical or different, can each be chosen from hydrogen atoms. As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

According to the invention, the structuring of the liquid fatty phase is obtained with the aid of at least one structuring polymer, such as the at least one polymer of formula (II). The at least one polyamide polymer of formula (II) may, for example, be in the form of a mixture of polymers, and this mixture may also comprise a compound of formula (II) wherein n is equal to zero, i.e., a diester.

Non-limiting examples of at least one polyamide polymer that may be used in the compositions of the present invention include the commercial products sold by Arizona Chemical under the names UNICLEAR 80 and UNICLEAR 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol. Another example of the ester-terminated polyamides represented by formula II is commercially available from Arizona Chemical under the name UNICLEAR VG (INCI name:ethylenediamine/stearyl dimer dilinoleate copolymer).

The structuring agent (e.g., non-wax polymer) may be present in an amount generally ranging from about 0.1% to about 40%, preferably from about 0.5% to about 20%, and more preferably from about 1% to about 10% by weight, relative to the total weight of the composition.

The composition according to the invention may also contain at least one fatty compound that is pasty at room temperature. For the purposes of the invention, the expression "pasty fatty substance" means a compound with a melting point ranging from 25 to 60° C. and preferably from 30 to 45° C. and/or a hardness ranging from 0.001 to 0.5 MPa and preferably from 0.005 to 0.4 MPa.

The melting point values correspond to the melting point measured using a differential scanning calorimeter (DSC), such as the calorimeter sold under the name DSC 2920 by the company TA Instruments, with a temperature rise of 5 or 10° C., per minute. (The melting point considered is the point corresponding to the temperature of the most endothermic peak in the thermogram.)

The hardness is measured according to a method of penetration of a probe into a sample of compound and in particular using a texture analyzer (for example the TA-XT2i from Rheo) equipped with a stainless steel cylinder 2 mm in diameter. The hardness measurement is performed at 20° C. at the center of 5 samples. The cylinder is introduced into each sample at a pre-speed of 1 mm/sec and then at a measuring speed of 0.1 mm/sec, the depth of penetration being 0.3 mm. The hardness value recorded is that of the maximum peak of the applied force.

Pasty fatty substances include hydrocarbon-based compounds, optionally of polymeric type; they may also be chosen from hydrocarbon-based compounds, silicone compounds and/or fluoro compounds, and mixtures thereof. Among the pasty compounds that may be mentioned are lanolins and lanolin derivatives, for instance acetylated lanolins or oxypropylenated lanolins, with a viscosity from 18 to 21 Pa·s and preferably 19 to 20.5 Pa·s, and/or a melting point from 30 to 45° C., and mixtures thereof. Esters of fatty acids or of fatty alcohols may also be used, especially those containing 20 to 65 carbon atoms (and having a melting point of about 20 to 35° C. and/or viscosity at 40° C. ranging from 0.1 to 40 Pa·s), for instance triisostearyl or cetyl citrate; arachidyl propionate; polyvinyl laurate, cholesterol esters, for instance triglycerides of plant origin such as hydrogenated plant oils, viscous polyesters, for instance poly(12-hydroxystearic acid), and mixtures thereof. Triglycerides of plant origin that may be used include hydrogenated castor oil derivatives, such as "Thixin R" from Rheox. Mention may also be made of silicone pasty fatty substances such as polydimethylsiloxanes (PDMS) containing pendant chains of the alkyl or alkoxy type containing from 8 to 24 carbon atoms, and having a melting point of 20-55° C, for instance stearyl dimethicones, especially those sold by the company Dow Corning under the trade names DC2503 and DC2-5514, and mixtures thereof.

The pasty fatty substance may be present in an amount of from 0.1 to 10% by weight, based on the weight of the composition.

In addition to water, the aqueous phase may contain a water-miscible solvent (miscibility in water of greater than 50% by weight at 25° C.), for instance, lower mono-alcohols containing from 1 to 5 carbon atoms such as ethanol or isopropanol, glycols containing from 2 to 8 carbon atoms, such as propylene glycol, ethylene glycol, butylene glycol or dipropylene glycol, C3-C4 ketones and C2-C4 aldehydes. The aqueous phase may be present in a content ranging from about 1% to about 95% by weight, relative to the total weight of the composition, in some embodiments from about 3% to about 70% by weight, and more preferably from about 5% to about 45%, 50%, 55% or 60% by weight.

The compositions of the invention may contain surfactants. Surfactants typically employed in the compositions of the present invention include anionic, nonionic and cationic surfactants. See, e.g., *Encyclopedia of Chemical Technology, KIRK-OTHMER*, volume 22, pp. 333-432, 3rd edition, 1979, Wiley, for the definition of the properties and (emulsifying) functions of the surfactants, in particular pp. 347-377 of this publication regarding anionic and nonionic surfactants. Examples of surfactants useful in the compositions of the invention are include as nonionic surfactants, fatty acids, fatty alcohols, polyethoxylated fatty alcohols or polyglycerolated fatty alcohols, such as polyethoxylated stearyl alcohols or cetylstearyl alcohols, esters of fatty acid and sucrose, and glucose alkyl esters, in particular polyoxyethylenated $C_1$-$C_6$ alkyl glucose fatty esters, and as anionic surfactants, $C_{16}$-$C_{30}$ fatty acids neutralized by amines, ammonia or the alkali metal salts thereof. Examples of cationic surfactants include quaternary amines, amine oxides and amines, e.g., alkyl amines, alkyl imidazolines, ethoxylated amines, quaternary compounds, and quaternized esters. Cationic surfactants may also provide a conditioning effect.

Surfactants are generally present in amounts ranging from about 1 to about 30% by weight, and in some other embodiments from about 3% to about 15% by weight, relative to the total weight of the composition.

Depending upon the nature of the inventive composition, controlling viscosity may be important from the standpoints of fast and easy application of the composition, as well as uniform coating. In the case of washable and waterproof mascara, for example, viscosity of washable mascara generally ranges from about 10 to about 60 pascal seconds (Pa·s), and preferably from about 20 to about 40 Pa·s, whereas viscosity of waterproof mascara generally ranges from about 10 to about 70 Pa·s, and preferably from about 10 to about 40 Pa·s. Viscosity is measured at 25° C. with a Rheomat RM 180 viscometer fitted with a No. 4 rotor, wherein the measurement is carried out after spinning the rotor for 10 minutes (after which time stabilization of the viscosity and of the rotor spin speed are observed), at a shear rate of $200 \, s^{-1}$.

Viscosity may be adjusted by adding a thickener. Representative examples include cellulose-based thickeners, for example, water-soluble cellulose-based thickeners, such as hydroxyethylcellulose, methylcellulose, hydroxypropylcellulose and carboxymethylcellulose. Among these thickeners, specific examples include alginates, maltodextrin, polysaccharide resins such as starch and its derivatives, hyaluronic acid and its salts, clays, and, in particular, montmorillonites, hectorites and laponites, crosslinked polyacrylic acids, such as the "Carbopol" products from the company Goodrich, the polyglyceryl (meth)acrylate polymers sold under the names "Hispagel" or "Lubragel" by the companies Hispano Quimica or Guardian, polyvinylpyrrolidone (PVP), polyvinyl alcohol, crosslinked acrylamide polymers and copolymers, such as those sold under the names "PAS 5161" or "Bozepol C" by the company Hoechst, "Sepigel 305" by the company SEPPIC, crosslinked methacryloyloxyethyltrimethylammonium chloride homopolymers sold under the name "Salcare SC95" by the company Allied Colloid, and associative polymers and, in particular, associative polyurethanes. Oil soluble thickening agents may also be used. See, U.S. Patent Publications 2003/0215413, 2005/0065046 and 2002/0028226.

The thickening agent is generally present in an amount ranging from about 0.05% to about 20% by weight, and preferably from about 0.5% to about 10% by weight.

The composition also may contain at least one hydrophilic or hydrophobic plasticizing agent (or plasticizer), chosen for its compatibility with the polymer or polymers and in a quantity such that it does not impair the sensitivity of the film to water. This agent may be water soluble or insoluble in water and possibly may exist in the form of an aqueous dispersion.

There may be cited in particular, alone or as a mixture, the usual plasticizers such as:
glycols and derivatives thereof such as diethylene glycol ethylether, diethylene glycol methylether, diethylene glycol butylether or even diethylene glycol hexylether, ethylene glycol ethylether, ethylene glycol butylether, ethylene glycol hexylether;
esters of glycerol;
the derivatives of propylene glycol and in particular propylene glycol phenylether, propylene glycol diacetate, dipropylene glycol butylether, tripropylene glycol butylether, propylene glycol methylether, dipropylene glycol ethylether, tripropylene glycol methylether and diethylene glycol methylether, propylene glycol butylether;
esters of acids, in particular carboxylic, such as citrates, phthalates, adipates, carbonates, tartrates, phosphates, sebaceates; and
oxyethylene derivatives such as oxyethylene oils, in particular vegetable oils such as castor oil; and silicone oils.

The quantity of plasticizing agent may be chosen by the person skilled in the art on the basis of his general knowledge, in such manner as to obtain a film having the desired mechanical properties, while preserving the composition of the cosmetically acceptable properties.

The compositions of the present invention may further comprise at least one suitable (e.g., cosmetically or dermatologically acceptable) additive or adjuvant, including, for example, but not limited to moisturizers, colorants, fillers, preservatives, chelators such as EDTA and salts thereof, antioxidants (e.g., BHT, tocopherol), essential oils, neutralizing agents, defoaming agents, emollients, vitamins, trace elements and essential fatty acids. These ingredients may be soluble or dispersible in the aqueous or the fatty phase.

Examples of moisturizers include sodium lactate, mannitol, amino acids, hyaluronic acid, lanolin, urea, petroleum jelly and mixtures thereof. Other examples include polyols such as glycerin, diglycerin, triglycerin, polyglycerin, polyethylene glycol, ethylene glycol, diethylene glycol, triethylene glycol, propylene glycol, dipropylene glycol, hexylene glycol, 1,3-butylene glycol, 1,4-butylene glycol and sorbitol. A preferred moisturizer is glycerin. Moisturizers may be present in the compositions of the present invention in amounts generally ranging from about 1.0% to about 15%, and in some cases, from about 2.0% to about 10% by weight of the composition.

Colorants useful in the present invention typically include lipophilic dyes, hydrophilic dyes, traditional pigments, and nacreous pigments, and mixtures thereof. The colorant may have any shape, such as, for example, spheroidal, oval, platelet, irregular, and mixtures thereof. Pigments may optionally be surface-treated e.g., with silicones, perfluorinated compounds, lecithin, and amino acids.

The liposoluble dyes include, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

The pigments may be chosen from white pigments, colored pigments, inorganic pigments, organic pigments, coated pigments, uncoated pigments, pigments having a micron size and pigments not having a micron size. Among the inorganic pigments that may be mentioned are titanium dioxide, optionally surface-treated, zirconium oxide, zinc oxide, cerium oxide, chromium oxide, manganese violet, ultramarine blue, chromium hydrate, and ferric blue. Among the organic pigments which may be mentioned are carbon black, pigments of D&C type, lakes based on cochineal carmine, lakes based on barium, lakes based on strontium, lakes based on calcium, and lakes based on aluminum.

The nacreous pigments may, for example, be chosen from white nacreous pigments such as mica coated with titanium and mica coated with bismuth oxychloride, colored nacreous pigments such as titanium mica with iron oxides, titanium mica with, for example, ferric blue and/or chromium oxide, titanium mica with an organic pigment of the type mentioned above, as well as nacreous pigments based on bismuth oxychloride, interferential pigments, and goniochromatic pigments.

Colorants can generally be present in an amount ranging from about 0.01% to about 30%, and in some embodiments, from about 5% to 10% relative to the total weight of the composition.

The compositions of the present invention may also contain dispersion enhancing agents such as polysaccharide resins, e.g., KM 13, available from KAMA International Corp. (Duluth, Ga.). Dispersion enhancing agents are especially preferred in pigmented products.

Fillers and mothers-of-pearl may also be added to the formulations e.g., to modify the texture of the composition and the matteness/gloss effect. Fillers should be understood to mean lamellar or non-lamellar, inorganic or synthetic, colorless or white particles. Mothers-of-pearl should be understood to mean iridescent particles produced especially by certain mollusks in their shell or else synthesized. Pearling agents that may be used in the practice of the invention include mica, iron oxides, titanium dioxide and any other pearling agent known in the cosmetic arts.

For example, fillers may be chosen from those that are well known to a person skilled in the art and that are commonly used in cosmetic compositions. Examples include talc, mica, silica, kaolin, polyamide powders, for instance Nylon® (Orgasol from Atochem), poly-β-alanine powders and polyethylene powders, tetrafluoroethylene polymer powders, for instance Teflon®, lauroyl lysine, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylate particles and silicone resin microbeads (for example Tospearls® from Toshiba), magnesium hydrocarbonate, hydroxyapatite, hollow silica microspheres (Silica Beads® from Maprecos), glass or ceramic microcapsules, metal soaps derived from carboxylic organic acids comprising from 8 to 22 carbon atoms, such as from 12 to 18 carbon atoms, for example zinc stearate, magnesium stearate, lithium stearate, zinc laurate and magnesium myristate, and mixtures thereof, chalk, Fuller's earth, sericite, muscovite, phlogopite, lepidolite, biotite, vermiculite, magnesium carbonate, calcium carbonate, aluminum silicate, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate, barium silicate, calcium silicate, magnesium silicate, strontium silicate, metal tungstate, magnesium, alumina, zeolite, barium sulfate, calcined calcium sulfate (calcined gypsum), calcium phosphate, colloidal silicone dioxide, boron nitride, cyclodextrin and benzoguanamine resin powder.

Filler(s) may be present in an amount ranging from about 0.1% to about 25%, for example, from about 1% to about 20% by weight of the total weight of the composition.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate(methylparaben), ethyl para-hydroxybenzoate(ethylparaben), propyl para-hydroxybenzoate(propylparaben), butyl para-hydroxybenzoate (butylparaben) and isobutyl para-hydroxybenzoate(isobutylparaben), imidazolidinyl urea and phenoxyethanol. Mixtures of preservatives may certainly be used, e.g., the mixture of methylparaben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa. Preservatives may be present in amounts generally ranging from about 0.01% to about 5% by weight of the composition.

The following examples are intended to further illustrate the present invention. They are not intended to limit the invention in any way. Unless otherwise indicated, all parts are by weight.

EXAMPLE 1

| Lengthening Mascara | | | |
|---|---|---|---|
| Seq | INCI Name | | |
| A1 | Beeswax | | 4.80 |
| | Glyceryl Stearate | | 4.00 |
| | Branched Kester BK-42 (Synthetic Alcohol Ester) | | 2.50 |
| | Carnauba wax | | 3.45 |
| | Stearic acid | | 3.00 |
| | Butylparaben | | 0.05 |
| | Ethylenediamine/stearyl dimer dilinoleate copolymer | | 3.00 |
| A2 | Polymethyl methacrylate | | 2.00 |
| | Black Iron Oxide | | 8.00 |
| B | Water | | 39.55 |
| | Hydroxyethyl cellulose | | 0.35 |
| | PVP K-30 | | 1.00 |
| | Butylene glycol | | 2.00 |
| | Methylparaben | | 0.40 |

-continued

Lengthening Mascara

| Seq | INCI Name | |
|---|---|---|
| | Triethanolamine | 1.50 |
| | Simethicone | 0.10 |
| C | Cyclopentasiloxane | 2.00 |
| | Cyclopentasiloxane/Dimethiconol | 3.00 |
| | Polyethylene | 2.00 |
| | Silica | 1.00 |
| D | Urethane-Acrylic Hybrid Polymer | 10.00 |
| E | Water | 1.00 |
| | Imidazolidinyl urea | 0.30 |
| F | Alcohol | 5.00 |
| | TOTAL | 100.00 |

To make the mascara, phase A1 ingredients were added to a main beaker with heating at 85-90° C., followed by addition of phase A2 and homogenizing for 1 hour. In a second beaker, water was added, followed by addition of hydroxyethylcellulose (at room temperature), while mixing to allow the hydroxyethylcellulose to hydrolyze. This mixture was heated to about 40-45° C., followed by addition of PVP K-30, with mixing until it was dispersed. In a third beaker, methylparaben was mixed with butylene glycol, with heating to about 40-45° C. to dissolve the methylparaben. Once clear, this solution was added to the second beaker with mixing. The resulting mixture in the second beaker was heated to about 85-90° C., followed by addition of triethanolamine and simethicone with mixing for about 5 minutes, followed by addition of another 20 g of water. While homogenizing, the ingredients of the second beaker were added to the main beaker. The temperature of both mixtures was 85-90° C. at the time they were mixed together. Emulsification was continued for about 20 minutes while maintaining temperature, followed by initiating cooling with a sweep mixer at slow speed. Phase C ingredients were pre-mixed and then added to the main batch at about 50-55° C., followed by addition of phase D at about 45-50° C. slowly. Phase E was added at 40° C., followed by addition of alcohol (phase F) at about 30-35° C., and then dropping the temperature of the batch slightly to 30-32° C.

EXAMPLE 2

Comparative Example

The inventive composition of example 1 was compared to the following commercial lengthening mascara from the standpoints of various rheological properties. These experiments are designed to measure the ability of the film formed on the eyelash by the mascara to stretch without breaking and to hold the additional length for a predetermined time. The experiments included measurement of critical yield stress (i.e., a dynamic strain amplitude sweep to measure the critical stress at which a film breaks and yields), the elastic modulus (G1) in the linear viscoelastic region, and the elastic modulus as a function of frequency or rate of deformation (i.e., a dynamic frequency sweep).

| Ingredient (CTFA Name) | % w/w |
|---|---|
| Triethanolamine | 1.50 |
| Glyceryl Stearate | 4.00 |
| Iron Oxides | 8.00 |

-continued

| Ingredient (CTFA Name) | % w/w |
|---|---|
| Acrylates Copolymer* | 10.00 |
| VP/Eicosene Copolymer | 3.00 |
| Dimethiconol and Cyclopentasiloxane | 3.00 |
| Cyclopentasiloxane | 2.00 |
| Stearic Acid** | 3.00 |
| Propylene Glycol | 2.00 |
| Alcohol Denatured | 5.00 |
| Silica | 1.00 |
| Water | 40.55 |
| Paraffin | 2.50 |
| Beeswax | 4.80 |
| Copernicia Cerifera (Carnauba) Wax | 3.45 |
| Simethicone | 0.10 |
| Polyethylene | 2.00 |
| PVP | 1.00 |
| Hydroxyethylcellulose | 0.35 |
| Polymethyl Methacrylate coated with Isopropyl Titanium Triisostearate | 2.00 |
| Preservatives | 0.75 |
| Total | 100.00 |

*Daitosol 5000 AD
**Blend of Stearic, Palmitic and Myristic Acids 1.59:1.32:0.09

The results are shown in Table 3 below.

TABLE 3

| | Critical Yield Stress | $G'$ (elastic modulus) in Linear Viscoelastic Region | $G'$ Elastic Modulus (Pascal) at 0.1 rad/sec | $G'$ Elastic Modulus (Pascal) at 100 rad/sec |
|---|---|---|---|---|
| Inventive Composition | 150 Pascal | 24,850 Pascal | 9316 | 39,535 |
| Commercial Lengthening Mascara | 38 Pascal | 9,703 Pascal | 5278 | 16,071 |

The results showed about a 4-fold difference in critical yield stress, nearly a 3-fold difference in elastic modulus in the linear viscoelastic region, and slightly less or greater than a 2-fold difference in elastic modulus at various frequencies. Collectively, these results are believed to show that the lengthening effect of the inventive mascara composition would be superior to the commercial formula.

All publications cited in the specification are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition for application to eyelashes, comprising an aqueous phase, a fatty phase, a structuring agent, and a polyurethane/poly(meth)acrylate graft copolymer, wherein the polyurethane/poly(meth)acrylate graft copolymer is an interpenetrated polymer network obtained by simultaneous polymerization or crosslinking of the two types of monomers, wherein the cosmetic composition for application to eyelashes is a mascara, wherein the structuring agent comprises at least one wax.

2. The composition of claim 1, wherein said copolymer is present as an aqueous dispersion of particles.

3. The composition of claim 2, wherein said particles have a weight-average size of between 90 and 110 nm and a number-average size of about 80 nm, and a glass transition temperature, Tg, ranging from about −60° C. to +100° C.

4. The composition of claim 3, wherein said poly(meth) acrylate comprises polymethyl methacrylate.

5. The composition of claim 1, wherein said copolymer is present in an amount of about 0.1% to about 20% by weight, relative to the total weight of the composition.

6. The composition of claim 1, wherein said copolymer is present in an amount of about 0.5% to about 15% by weight, relative to the total weight of the composition.

7. The composition of claim 1, wherein copolymer is present in an amount of about 1% to about 10% by weight, relative to the total weight of the composition.

8. The composition of claim 1, wherein said wax comprises tetradecyl-octadecanyl-behenate or hexadecyl-cosanyl-hexacosanate.

9. The composition of claim 8, wherein said wax is present in an amount of about 0.1% to about 40% by weight, relative to the total weight of the composition.

10. The composition of claim 8, wherein said wax is present in an amount of about 0.5% to about 20% by weight, relative to the total weight of the composition.

11. The composition of claim 8, wherein said wax is present in an amount of about 1% to about 10% by weight, relative to the total weight of the composition.

12. The composition of claim 1, comprising at least two waxes.

13. The composition of claim 1 or 8, wherein said structuring agent further comprises a non-wax polymer.

14. The composition of claim 13, wherein said polymer comprises an ester-terminated polyamide represented by formula (II)

$$R^1-O-\left[\underset{O}{\overset{\parallel}{C}}-R^2-\underset{O}{\overset{\parallel}{C}}-\underset{\underset{R^4}{\vert}}{N}-R^3-\underset{\underset{R^4}{\vert}}{N}\right]_n-\underset{O}{\overset{\parallel}{C}}-R^2-\underset{O}{\overset{\parallel}{C}}-O-R^1$$

wherein: n is an integer which represents the number of amide units such that the number of ester groups present in the structuring polymer ranges from 10% to 50% of the total number of all the ester groups and all the amide groups comprised in the structuring polymer;

$R^1$, which are identical or different, are each chosen from alkyl groups comprising at least 4 carbon atoms and alkenyl groups comprising at least 4 carbon atoms;

$R^2$, which are identical or different, are each chosen from $C_4$ to $C_{42}$ hydrocarbon-based groups with the proviso that at least 50% of $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$ —N—$R^3$, with the proviso that at least 50% of all $R^4$ are chosen from hydrogen atoms.

15. The composition of claim 13, wherein said polymer comprises an ethylenediamine/stearyl dimer dilinoleate copolymer.

16. The composition of claim 1, further comprising a colorant.

17. The composition of claim 16, wherein said colorant is present in an amount of about 5% to about 10% by weight, relative to the total weight of the composition.

18. The composition of claim 1, further comprising a filler.

19. A method of lengthening eye lashes comprising applying to eyelashes a cosmetic composition according to claim 1.

20. A method for making a mascara composition, comprising mixing an aqueous phase, a fatty phase, a structuring agent, and a polyurethane/poly(meth)acrylate graft copolymer, wherein the polyurethane/poly(meth)acrylate graft copolymer is an interpenetrated polymer network obtained by simultaneous polymerization or crosslinking of the two types of monomers, wherein the cosmetic composition for application to eyelashes is a mascara, and wherein the structuring agent comprises at least one wax.

\* \* \* \* \*